(12) United States Patent (10) Patent No.: US 7,740,579 B2
Silverbrook et al. (45) Date of Patent: Jun. 22, 2010

(54) OTOSCOPE WITH INTERNAL PRINTER

(75) Inventors: Kia Silverbrook, Balmain (AU); Janette Faye Lee, Balmain (AU)

(73) Assignee: Silverbrook Research Pty Ltd, Balmain, New South Wales (AU)

( * ) Notice: Subject to any disclaimer, the term of this patent is extended or adjusted under 35 U.S.C. 154(b) by 1037 days.

(21) Appl. No.: 10/451,722

(22) PCT Filed: Nov. 22, 2001

(86) PCT No.: PCT/AU01/01513

§ 371 (c)(1),
(2), (4) Date: Jun. 23, 2003

(87) PCT Pub. No.: WO02/49504

PCT Pub. Date: Jun. 27, 2002

(65) Prior Publication Data

US 2004/0049098 A1 Mar. 11, 2004

(30) Foreign Application Priority Data

Dec. 21, 2000 (AR) ..................... PR2241

(51) Int. Cl.
*A61B 1/267* (2006.01)
(52) U.S. Cl. ............. 600/200; 600/104; 600/105; 600/106; 600/129; 600/153; 347/2; 347/85; 347/86; 347/87; 351/205; 351/206; 351/218; 351/221; 400/76; 400/613
(58) Field of Classification Search .................. 600/200
See application file for complete search history.

(56) References Cited

U.S. PATENT DOCUMENTS

| | | | | |
|---|---|---|---|---|
| 4,688,582 A | * | 8/1987 | Heller et al. | 600/559 |
| 5,047,870 A | * | 9/1991 | Filo | 358/472 |
| 5,279,304 A | * | 1/1994 | Einhorn et al. | 600/537 |
| 5,363,839 A | | 11/1994 | Lankford | |
| 5,493,409 A | * | 2/1996 | Maeda et al. | 358/296 |
| 5,757,388 A | * | 5/1998 | Stephenson | 347/2 |
| 5,785,644 A | * | 7/1998 | Grabover et al. | 600/131 |
| 5,798,774 A | | 8/1998 | Okada et al. | |
| 5,879,289 A | | 3/1999 | Yarush et al. | |
| 5,919,130 A | | 7/1999 | Monroe et al. | |
| 5,999,203 A | * | 12/1999 | Cane et al. | 347/171 |
| 6,106,457 A | * | 8/2000 | Perkins et al. | 600/175 |
| 6,152,619 A | * | 11/2000 | Silverbrook | 400/88 |
| 6,270,271 B1 | * | 8/2001 | Fujiwara | 400/693 |
| 7,073,717 B1 | * | 7/2006 | Arnold et al. | 235/472.01 |
| 7,098,941 B2 | * | 8/2006 | Miyazaki et al. | 348/207.2 |

FOREIGN PATENT DOCUMENTS

| | | |
|---|---|---|
| EP | 0848540 A | 6/1998 |
| EP | 0 868 878 A1 | 10/1998 |
| WO | WO 99/04368 | 1/1999 |
| WO | WO 99/55218 | 11/1999 |
| WO | WO 00/30526 | 6/2000 |

* cited by examiner

*Primary Examiner*—Matthew J Kasztejna

(57) ABSTRACT

An otoscope 800 includes a lens 802 and an eyepiece 801 by which a doctor can examine the external ear cavity of a patient. The otoscope includes a handle 803 within which there is situated a printer to provide an instantaneous permanent record of an image viewed by the doctor. Upon activation of a trigger 817, a permanent graphic image is printed onto a sheet 816 that passes out of the handle 803 via slot 804.

4 Claims, 11 Drawing Sheets

OTOSCOPE WITH INTERNAL PRINTER

CROSS REFERENCES TO RELATED APPLICATIONS

The present application is a 371 of PCT/AU01/01513 filed on Nov. 22, 2001.

FIELD OF THE INVENTION

The following invention relates to a device having an in-built image sensor and an internal print engine. More particularly, the invention relates to an otoscope having an internal printer.

Conventional otoscopes include a lens associate with an eyepiece through which a doctor views the external ear cavity of a patient. Such devices also include a battery-operated light source to illuminate the external ear cavity for viewing by the doctor.

It would be beneficial to both doctor and patient if a permanent graphic record of the appearance of the external ear cavity could be provided inexpensively and instantaneously. This might be achieved by a hand-held otoscope having an internal printer adapted to print a graphic image of the external ear cavity as observed by a doctor with the otoscope.

DISCLOSURE OF THE INVENTION

There is disclosed herein a hand-held otoscope having a built-in printer for printing a graphic image of an external ear cavity as received by the otoscope.

Preferably the printer is built into a handle of the otoscope.

Preferably the otoscope includes an image sensor associated with a print engine controller which controls a print head.

Preferably associated with the image sensor and print engine controller is a micro-control circuit adapted to control a motor driver for print media transportation and a motor driver for operation of a guillotine motor for severing a printed image from a roller of print media.

Preferably associated with the print engine controller is an image memory.

Preferably the print head is a monolithic pagewidth print head.

Preferably the print head is an ink jet print head.

Preferably the otoscope includes a light source for illuminating the external ear cavity of a patient for viewing by a doctor with the otoscope.

Preferably the printer includes a print engine assembly comprising first and second sub-assemblies, the first sub-assembly incorporating an ink source and print media and the second sub-assembly incorporating a print head.

BRIEF DESCRIPTION OF THE DRAWINGS

The invention will now be described by way of example with reference to the accompanying diagrammatic drawings in which.

DESCRIPTION OF THE PREFERRED EMBODIMENT

Figure 1:
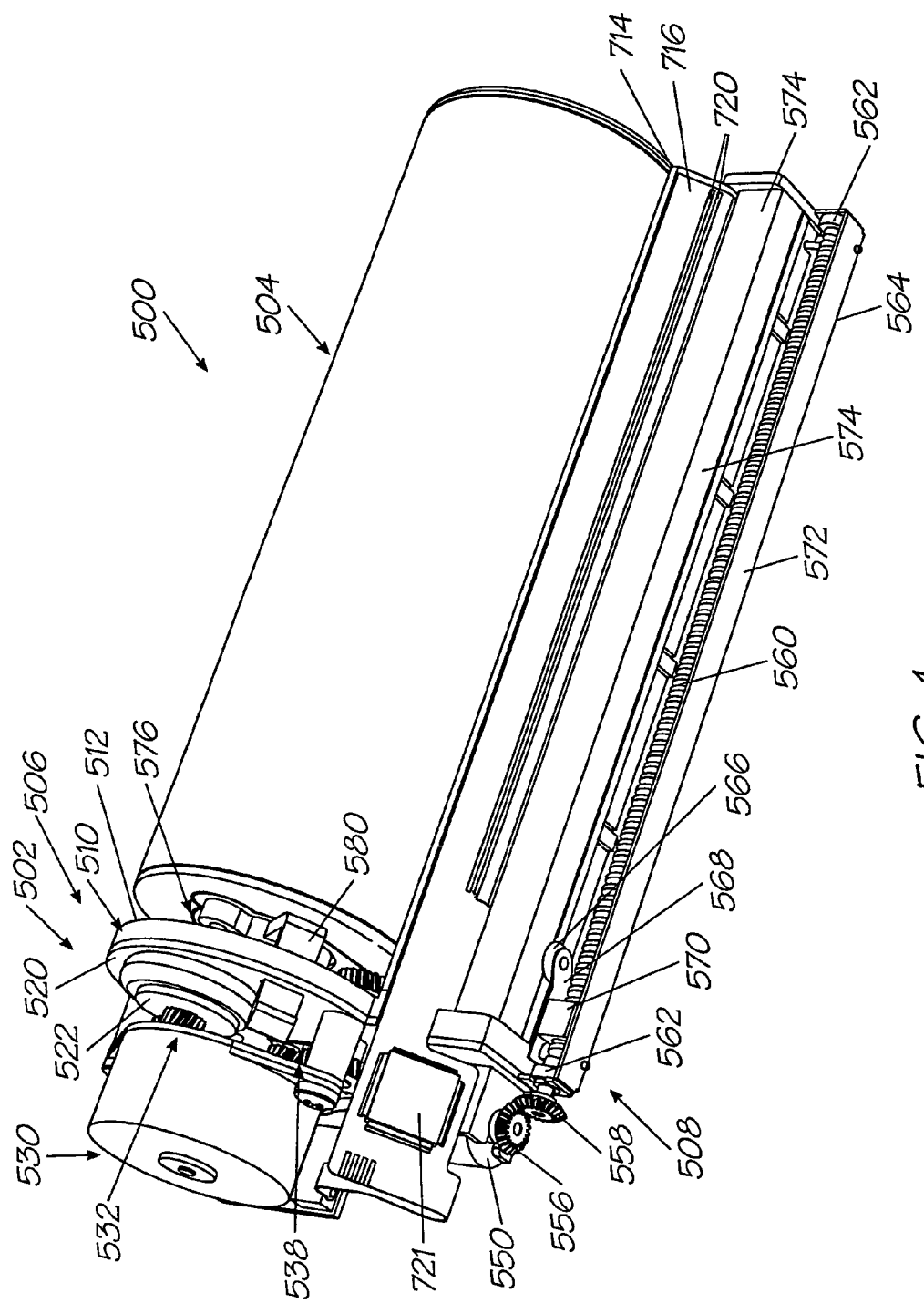
FIG. 1 shows a three dimensional view of a print engine, including components in accordance with the invention.
Figure 2:
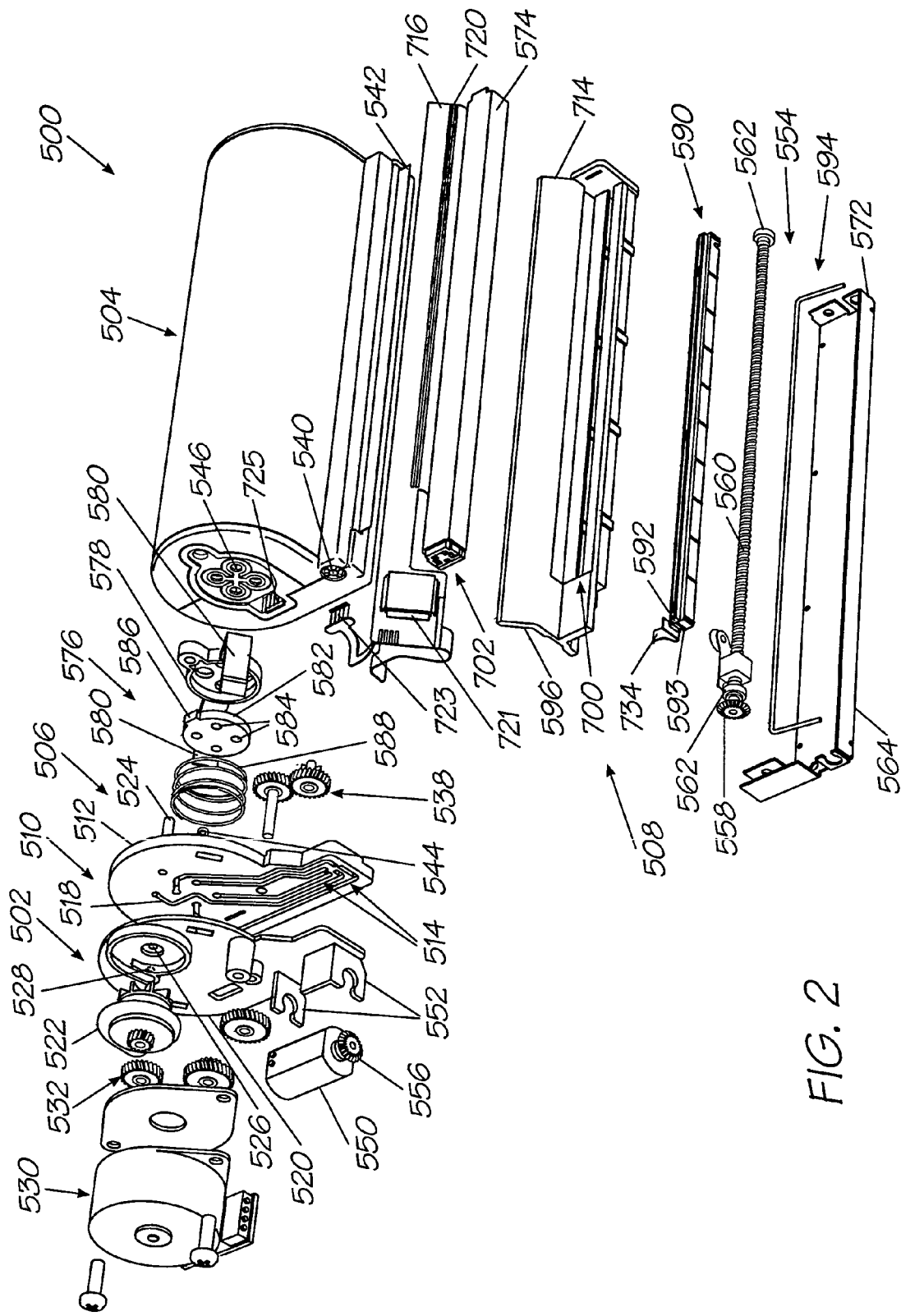
FIG. 2 shows a three dimensional, exploded view of the print engine.

In FIGS. 1 to 10 of the accompanying drawings, reference numeral 500 generally designates a print engine, in accordance with the invention. The print engine 500 includes a print engine assembly 502 on which a print roll cartridge 504 is removably mountable.

The print cartridge 504 is described in greater detail in our co-pending applications PCT/AU00/00741 and PCT/AU00/742, the contents of that disclosure being specifically incorporated herein by reference.

The print engine assembly 502 comprises a first sub-assembly 506 and a second, print head sub-assembly 508.

The sub-assembly 506 includes a chassis 510. The chassis 510 comprises a first molding 512 in which ink supply channels 514 are molded. The ink supply channels 514 supply inks from the print cartridge 504 to a print head 516 {FIGS. 5 to 7) of the print head sub-assembly 508. The print head 516 prints in four colors or three colors plus ink which is visible in the infra-red light spectrum only (hereinafter referred to as 'infra-red ink'). Accordingly, four ink supply channels 514 are defined in the molding 512 together with an air supply channel 518. The air supply channel 518 supplies air to the print head 516 to inhibit the build up of foreign particles on a nozzle guard of the print head 516.

The chassis 510 further includes a cover molding 520. The cover molding 520 supports a pump 522 thereon. The pump 522 is a suction pump, which draws air through an air filter in the print cartridge 504 via an air inlet pin 524 and an air inlet opening 526. Air is expelled through an outlet opening 528 into the air supply channel 518 of the chassis 510.

The chassis 510 further supports a first drive motor in the form of a stepper motor 530. The stepper motor 530 drives the pump 522 via a first gear train 532. The stepper motor 530 is also connected to a drive roller 534 (FIG. 5) of a roller assembly 536 of the print cartridge 504 via a second gear train 538. The gear train 538 engages an engageable element 540 (FIG. 2) carried at an end of the drive roller 534. The stepper motor 530 thus controls the feed of print media 542 to the print head 516 of the sub-assembly 508 to enable an image to be printed on the print media 542 as it passes beneath the print head 516. It also to be noted that, as the stepper motor 530 is only operated to advance the print media 542, the pump 522 is only operational to blow air over the print head 516 when printing takes place on the print media 542.

The molding 512 of the chassis 510 also supports a plurality of ink supply conduits in the form of pins 544 which are in communication with the ink supply channels 514. The ink supply pins 544 are received through an elastomeric collar assembly 546 of the print cartridge 504 for drawing ink from ink chambers or reservoirs 548 (FIG. 5) in the print cartridge 504 to be supplied to the print head 516.

A second motor 550, which is a DC motor, is supported on the cover molding 520 of the chassis 510 via clips 552. The motor 550 is provided to drive a separating means in the form of a cutter arm assembly 554 to part a piece of the print media 542, after an image has been printed thereon, from a remainder of the print media. The motor 550 carries a beveled gear 556 on an output shaft thereof. The beveled gear 556 meshes with a beveled gear 558 carried on a worm gear 560 of the cutter assembly 554. The worm gear 560 is rotatably supported via bearings 562 in a chassis base plate 564 of the print head sub-assembly 508.

The cutter assembly 554 includes a cutter wheel 566, which is supported on a resiliently flexible arm 568 on a mounting block 570. The worm gear 560 passes through the mounting block 570 such that, when the worm gear 560 is rotated, the mounting block 570 and the cutter wheel 566 traverse the chassis base plate 564. The mounting block 570 bears against a lip 572 of the base plate 564 to inhibit rotation of the mounting block 570 relative to the worm gear 560. Further, to effect cutting of the print media 542, the cutter wheel 566 bears against an upper housing or cap portion 574 of the print head sub-assembly 508. This cap portion 574 is a metal portion. Hence, as the cutter wheel 566 traverses the capped portion 574, a scissors-like cutting action is imparted to the print media to separate that part of the print media 542 on which the image has been printed.

The sub-assembly 506 includes an ejector mechanism 576. The ejector mechanism 576 is carried on the chassis 510 and has a collar 578 having clips 580, which clip and affix the ejector mechanism 576 to the chassis 510. The collar 578 supports an insert 582 of an elastomeric material therein. The elastomeric insert 582 defines a plurality of openings 584. The openings 584 close off inlet openings of the pins 544 to inhibit the ingress of foreign particles into the pins 544 and, in so doing, into the channels 514 and the print head 516. In addition, the insert 584 defines a land or platform 586 which closes off an inlet opening of the air inlet pin 524 for the same purposes.

Figure 3:
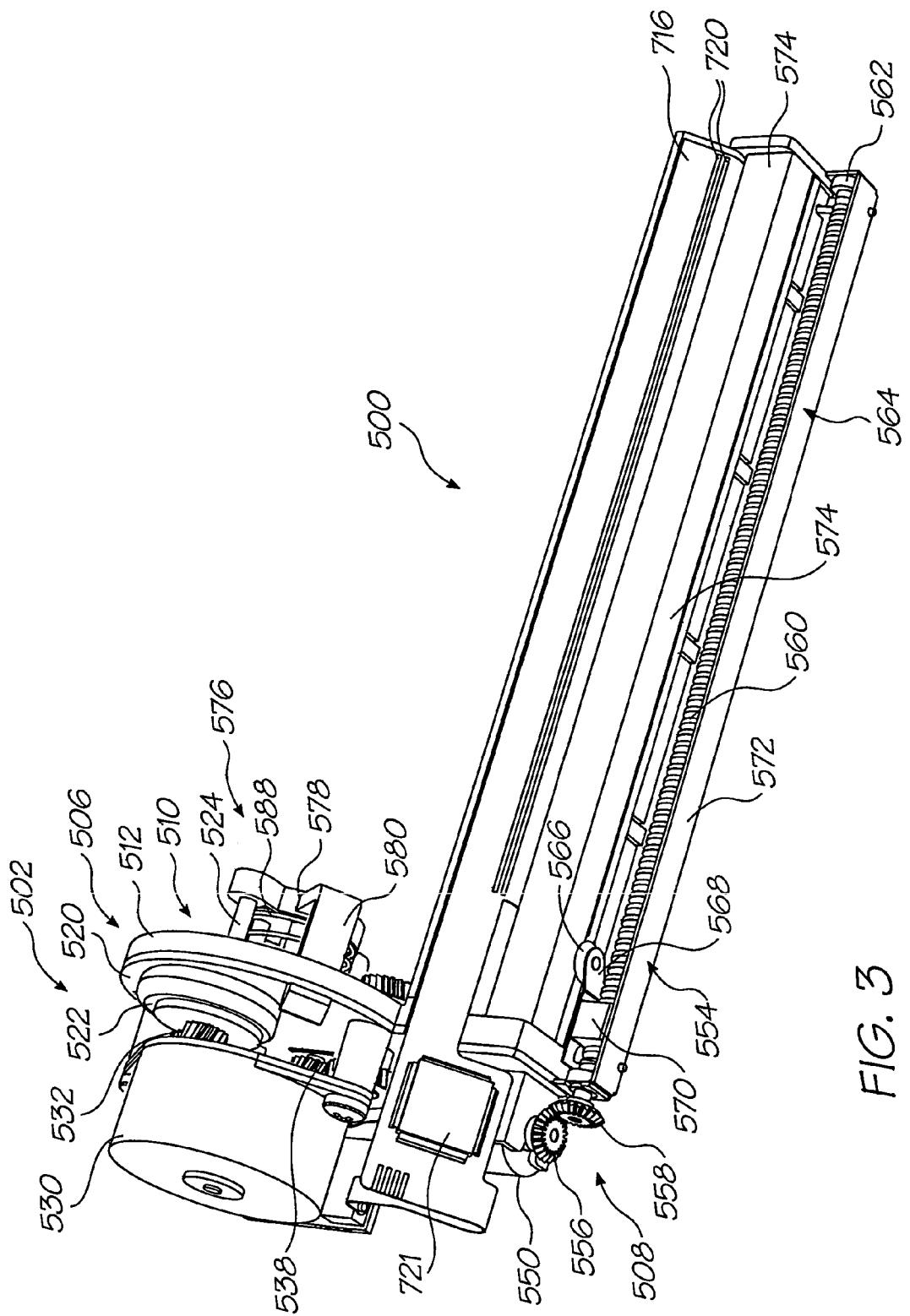
FIG. 3 shows a three dimensional view of the print engine with a removable print cartridge used with the print engine removed.
Figure 4:
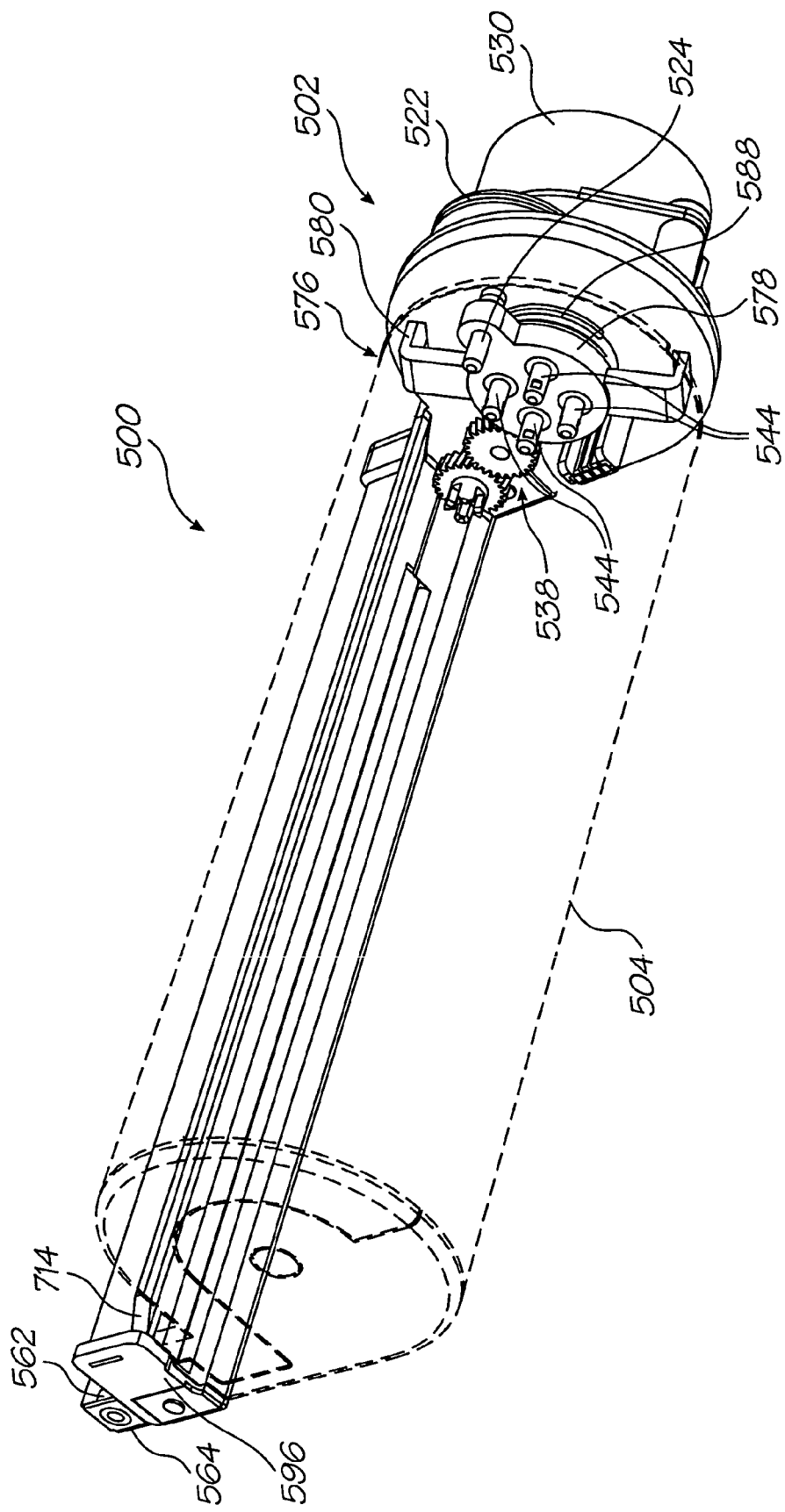
FIG. 4 shows a three dimensional, rear view of the print engine with the print cartridge shown in dotted lines.
Figure 5:
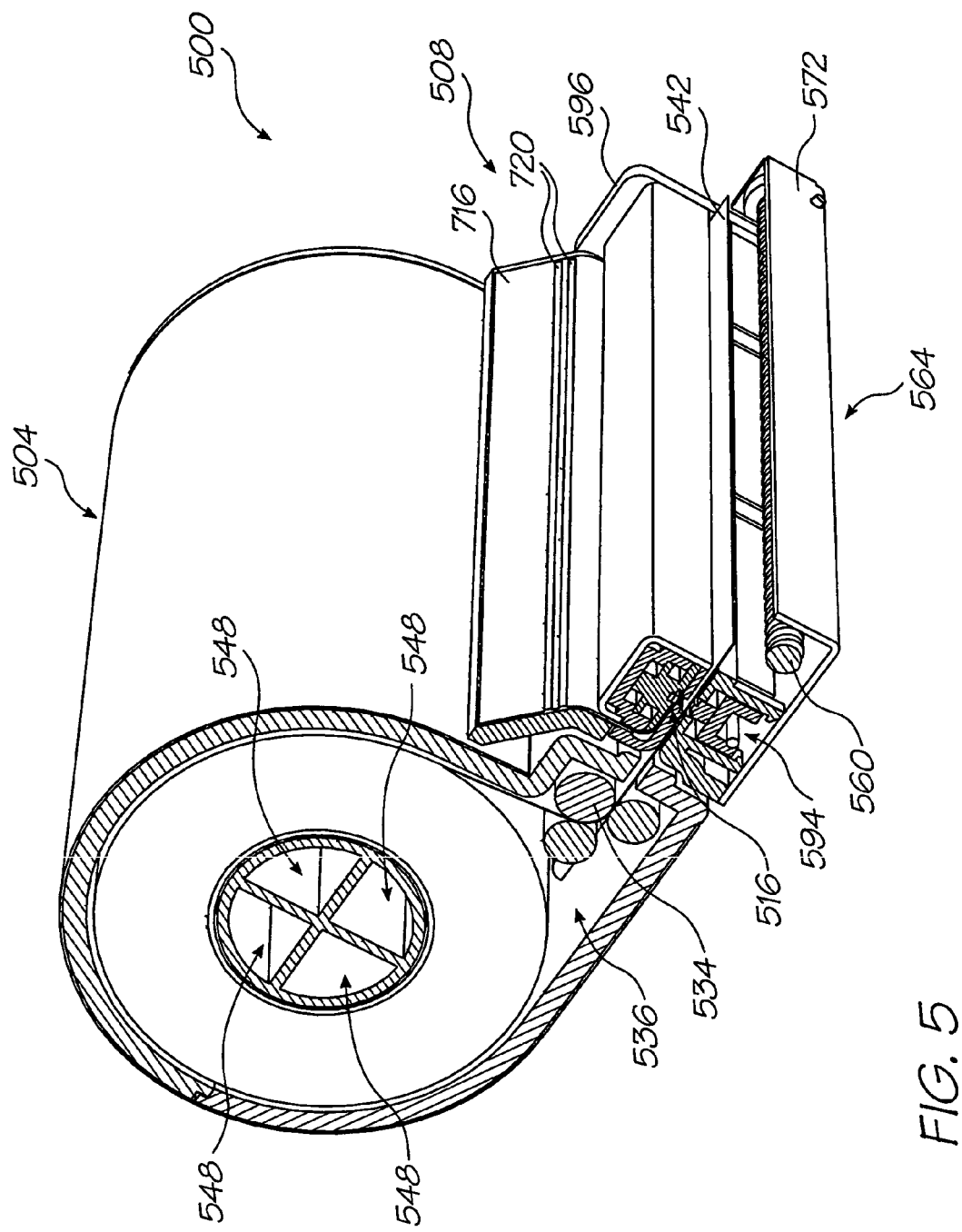
FIG. 5 shows a three dimensional, sectional view of the print engine.
Figure 6:
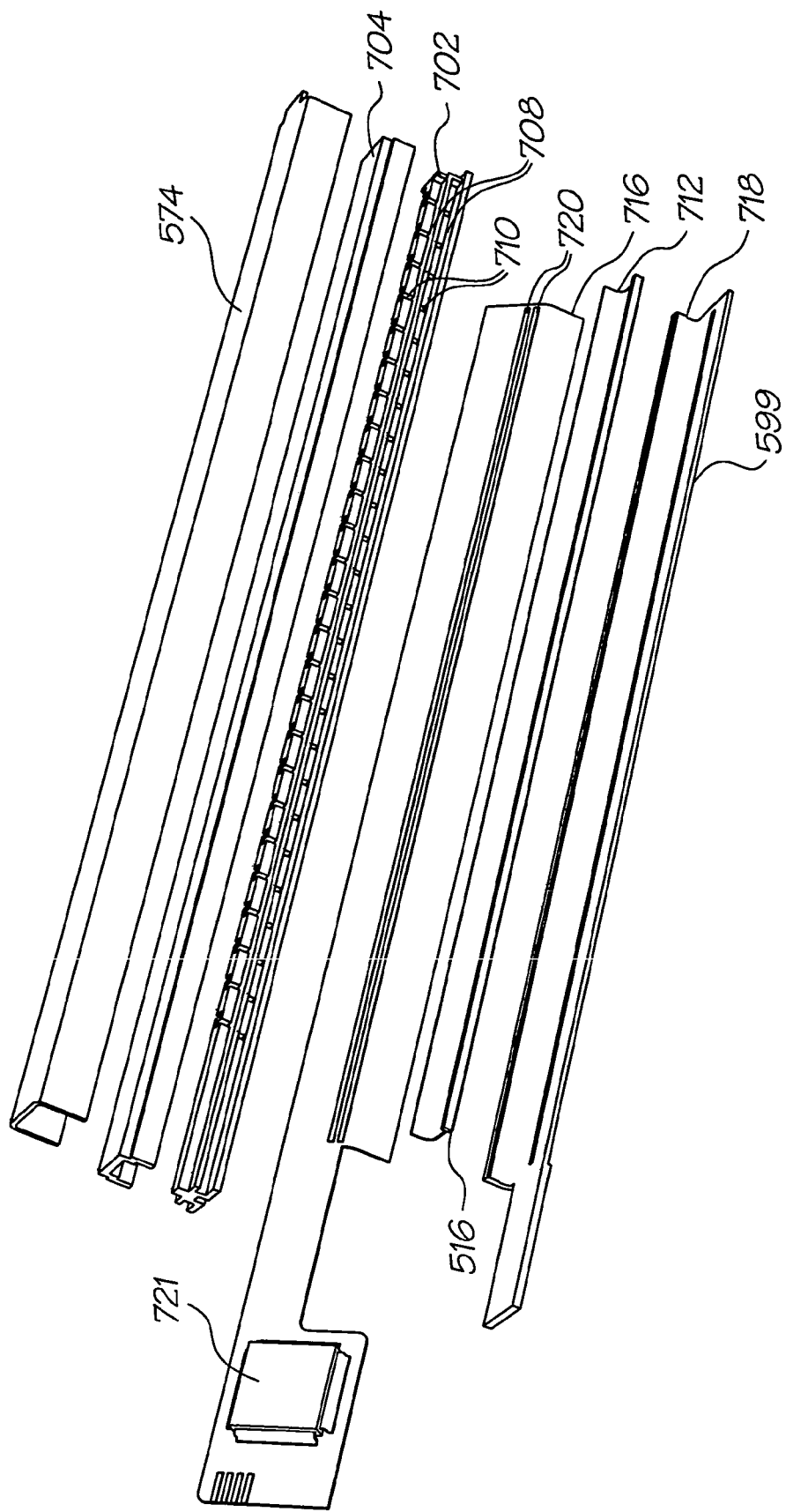
FIG. 6 shows a three dimensional, exploded view of a print head sub-assembly of the print engine.

A coil spring 588 is arranged between the chassis 510 and the collar 578 to urge the collar 578 to a spaced position relative to the chassis 510 when the cartridge 504 is removed from the print engine 500, as shown in greater detail in FIG. 3 of the drawings. The ejector mechanism 576 is shown in its retracted position in FIG. 4 of the drawings.

The print head sub-assembly 508 includes, as described above, the base plate 564. A capping mechanism 590 is supported displaceably on the base plate 564 to be displaceable towards and away from the print head 516. The capping mechanism 590 includes an elongate rib 592 arranged on a carrier 593. The carrier is supported by a displacement mechanism 594, which displaces the rib 592 into abutment with the print head 516 when the print head 516 is inoperative. Conversely, when the print head 516 is operational, the displacement mechanism 594 is operable to retract the rib 592 out of abutment with the print head 516.

The print head sub-assembly 508 includes a print head support molding 596 on which the print head 516 is mounted. The molding 596, together with an insert 599 arranged in the molding 596, defines a passage 598 through which the print media 542 passes when an image is to be printed thereon. A groove 700 is defined in the molding 596 through which the capping mechanism 590 projects when the capping mechanism 590 is in its capping position.

An ink feed arrangement 702 is supported by the insert 599 beneath the cap portion 574. The ink feed arrangement 702 comprises a spine portion 704 and a casing 706 mounted on the spine portion 704. The spine portion 704 and the casing 706, between them, define ink feed galleries 708 which are in communication with the ink supply channels 514 in the chassis 510 for feeding ink via passages 710 (FIG. 7) to the print head 516.

An air supply channel 711 (FIG. 8) is defined in the spine portion 704, alongside the print head 516.

Electrical signals are provided to the print head 516 via a TAB film 712 which is held captive between the insert 599 and the ink feed arrangement 702.

The molding 596 includes an angled wing portion 714. A flexible printed circuit board (PCB) 716 is supported on and secured to the wing portion 714. The flex PCB 716 makes electrical contact with the TAB film 712 by being urged into engagement with the TAB film 712 via a rib 718 of the insert 599. The flex PCB 716 supports busbars 720 thereon. The busbars 720 provide power to the print head 516 and to the other powered components of the print engine 500. Further, a camera print engine control chip 721 is supported on the flex PCB 716 together with a QA chip (not shown) which authenticates that the cartridge 504 is compatible and compliant with the print engine 500. For this purpose, the PCB 716 includes contacts 723, which engage contacts 725 in the print cartridge 504.

Figure 7:
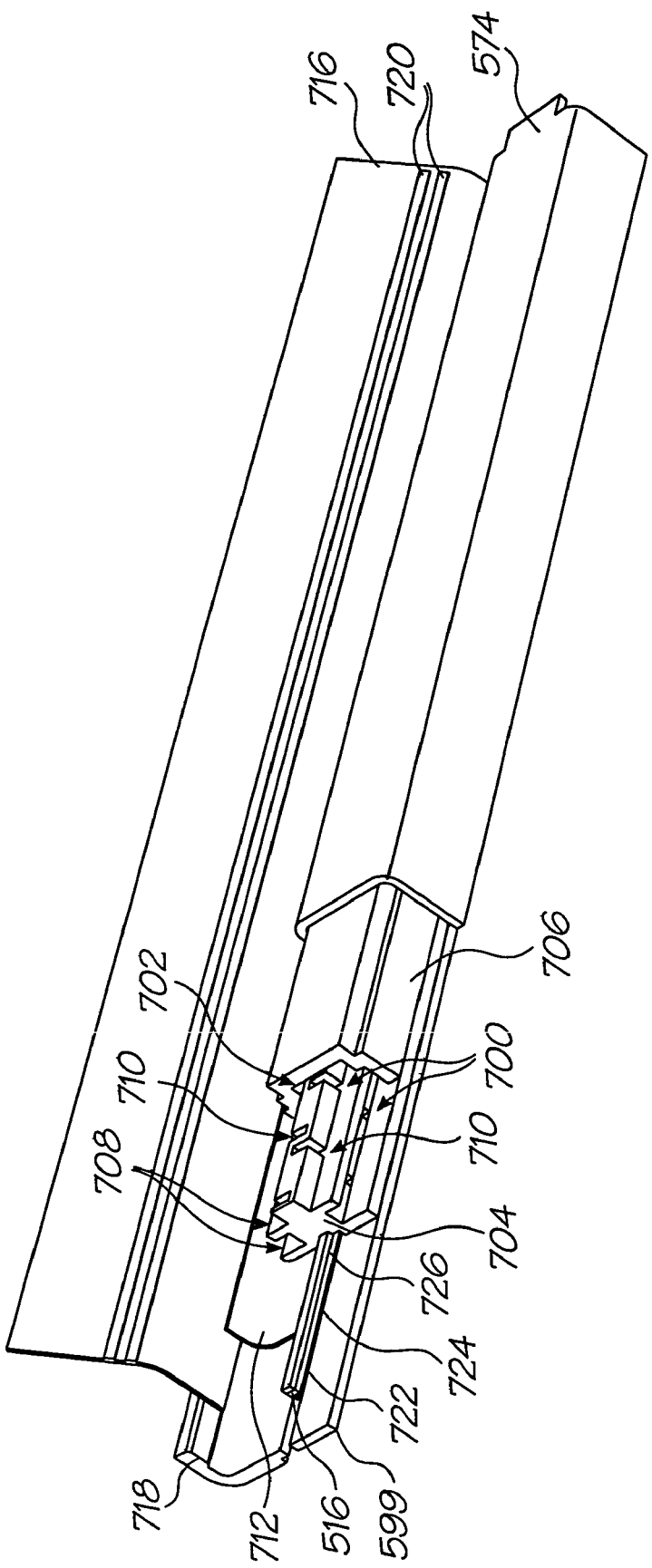
FIG. 7 shows a partly cutaway view of the print head sub-assembly.
Figure 8:
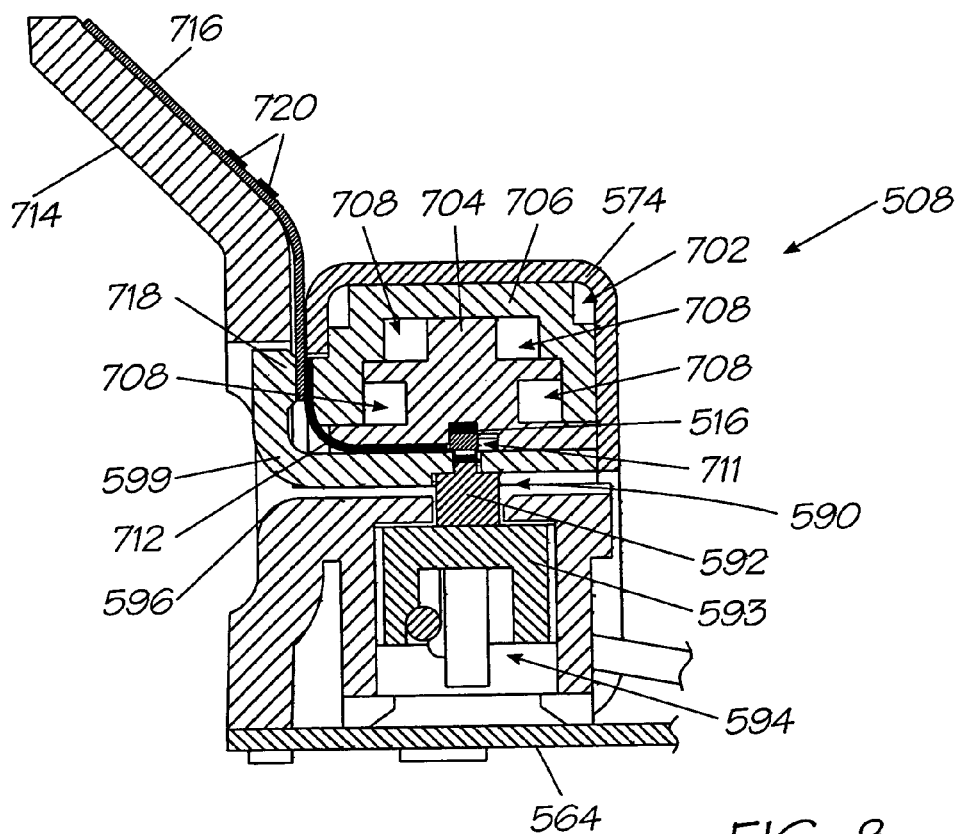
FIG. 8 shows a sectional end view of the print head sub-assembly with a capping mechanism in a capping position.
Figure 9:
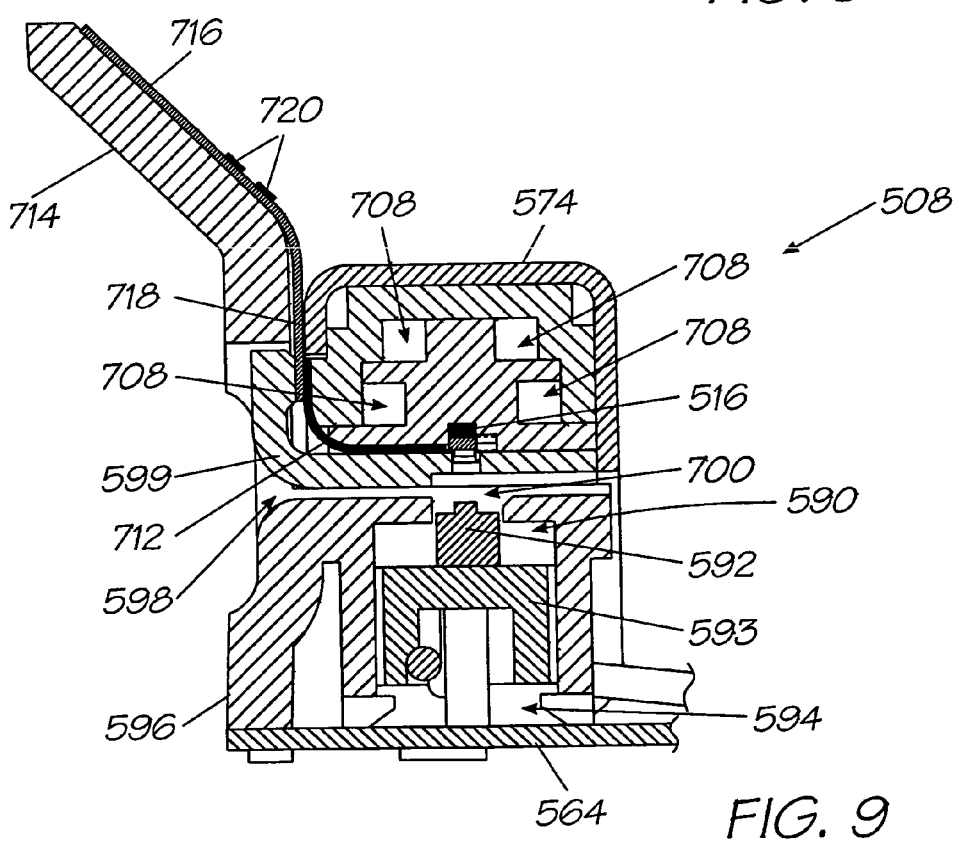
FIG. 9 shows the print head sub-assembly with the capping mechanism in its uncapped position.

As illustrated more clearly in FIG. 7 of the drawings, the print head itself includes a nozzle guard 722 arranged on a silicon wafer 724. The ink is supplied to a nozzle array (not shown) of the print head 516 via an ink supply member 726. The ink supply member 726 communicates with outlets of the passages 710 of the ink feed arrangement 702 for feeding ink to the array of nozzles of the print head 516, on demand.

Figure 10:
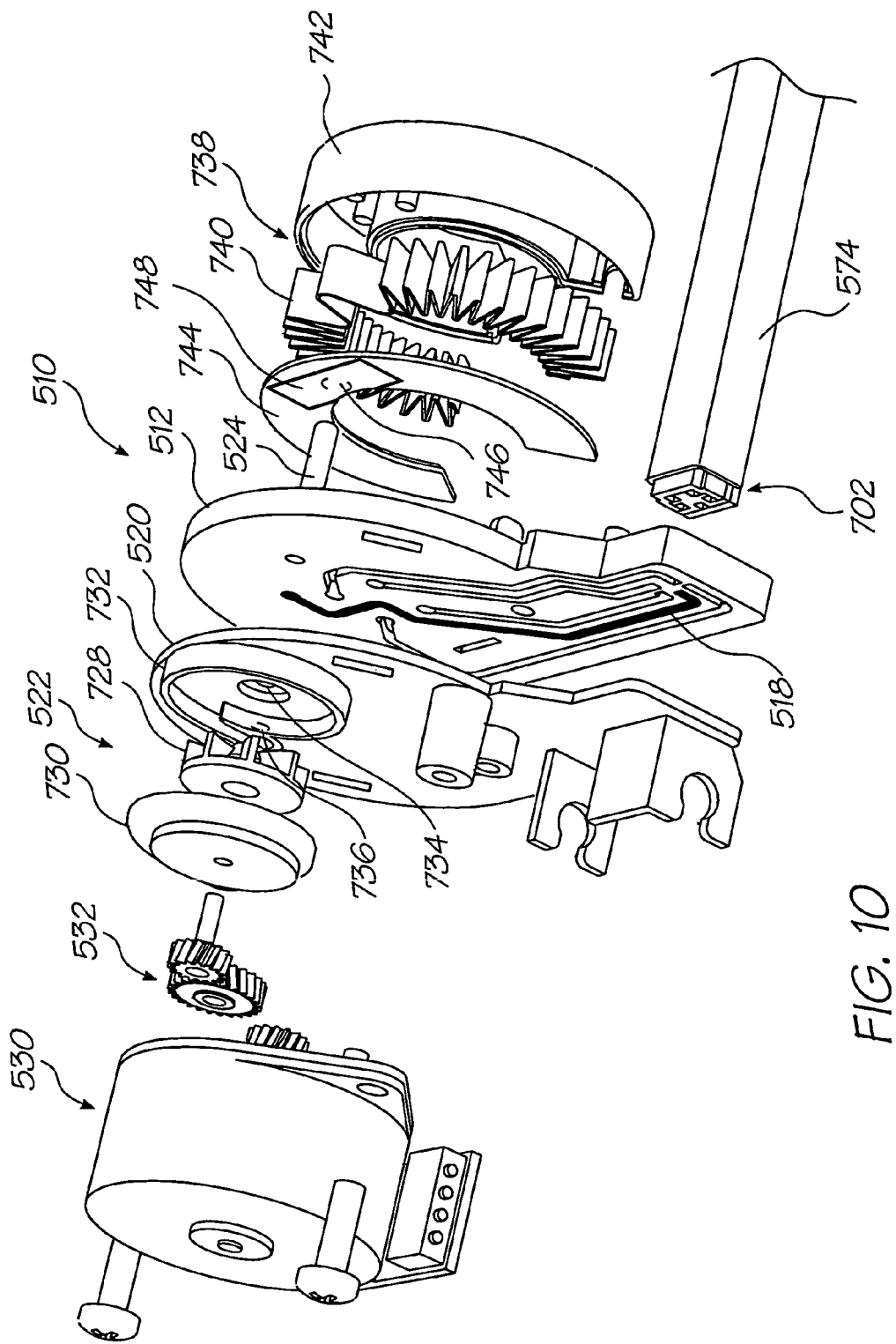
FIG. 10 shows an exploded, three dimensional view of an air supply arrangement of the print engine.

In FIG. 10, the air supply path for supplying air to the print head 516 is shown in greater detail. As illustrated, the pump 522 includes an impeller 728 closed off by an end cap 730. The cover molding 520 of the chassis forms a receptacle 732 for the impeller 728. The cover molding 520 has the air inlet opening 734 and the air outlet opening 736. The air inlet opening 734 communicates with the pin 524. The air outlet opening 736 feeds air to the air supply channel 518 which, in FIG. 10, is shown as a solid black line. The air fed from the air supply channel 518 is blown into the print head 516 to effect cleaning of the print head. The air drawn in via the pump 522 is filtered by an air filter 738, which is accommodated in the print cartridge 504. The air filter 738 has a filter element 740 which may be paper based or made of some other suitable filtering media. The filter element 740 is housed in a canister, having a base 742 and a lid 744. The lid 744 has an opening 746 defined therein. The opening 746 is closed off by a film 748 which is pierced by the pin 524. The advantage of having the air filter 738 in the print cartridge 504 is that the air filter 738 is replaced when the print cartridge 504 is replaced.

It is an advantage of the invention that an air pump 522 is driven by the stepper motor 530, which also controls feed of the print media to the print head 516. In so doing, fewer components are required for the print engine 500 rendering it more compact. In addition, as the same motor 530 is used for operating the air pump 522 and for feeding the print media 542 to the print head 516, fewer power consuming components are included in the print engine 500 rendering it more compact and cheaper to produce.

It is also to be noted that, in order to make the print engine 500 more compact, the size of the print engine assembly 502 is such that most of the components of the assembly 502 are received within a footprint of an end of the print cartridge 504.

Figure 11:
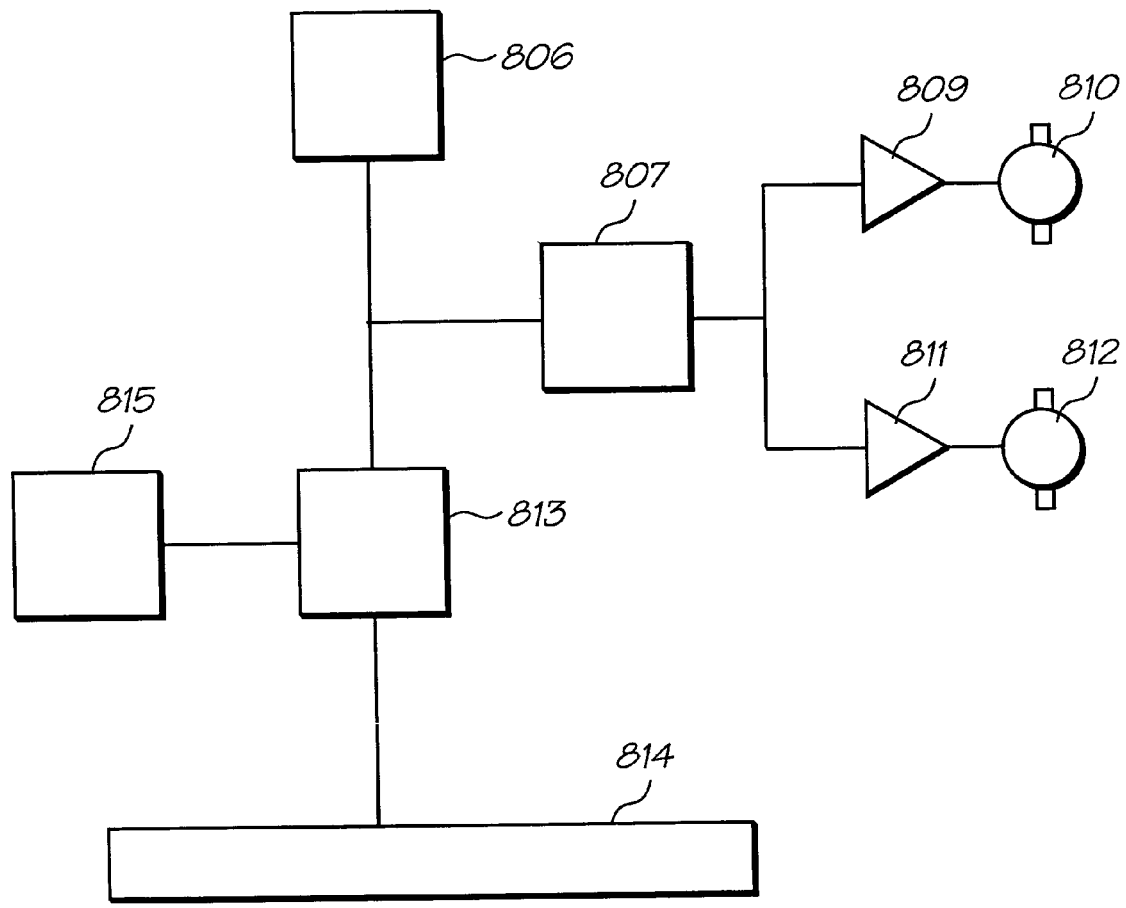
FIG. 11 is a schematic block diagram of components incorporated into an otoscope having a built-in printer.
Figure 12:
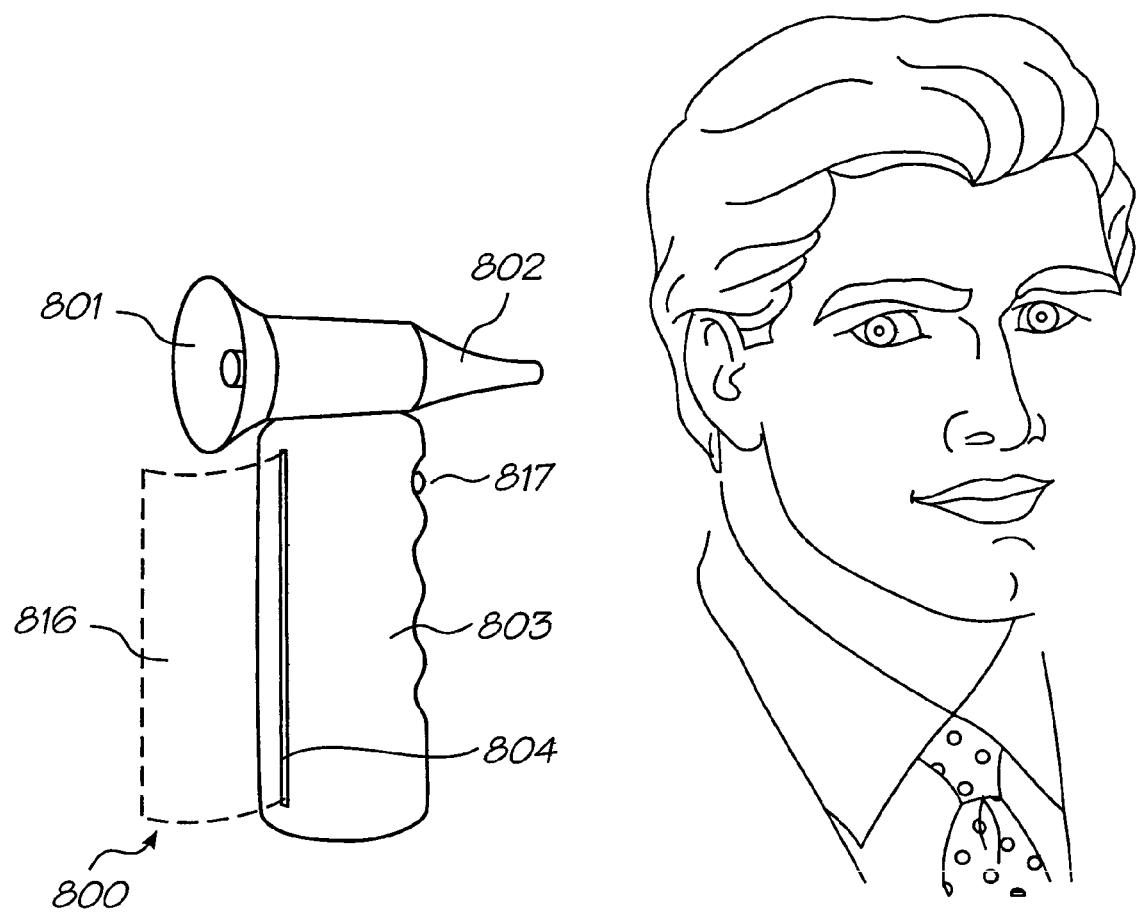
FIG. 12 is a schematic perspective view of an otoscope having a printer built into its handle.

In FIG. 11 there is schematically depicted in block diagram form the key internal components of an otoscope having an internal printer. The printer would typically utilize a monolithic print head 814 which could be the same as described above with reference to FIGS. 1 to 10, but could alternatively be another compact print head capable of printing on photograph-sized print media. An image sensor 806 receives images from a lens 802 (FIG. 12) of the otoscope. Image data from the image sensor 806 is fed to a print engine controller 813 which controls the print head 814. A memory 815 is associated with the print engine controller and stores an image memory. This image memory might be stored upon depression of a trigger 817 for example.

A micro-controller 807 associated with the image sensor and print engine controller controls a motor driver 809 which in turn drives a media transport device 810. This might be the same as stepper motor 530 described earlier.

The micro-controller 807 also controls a motor driver 811 which in turn controls a guillotine motor 812 to sever a printed sheet from an in-built roll of print media after an image is printed. A sheet being driven by media transport device 810 is shown in dotted lines at 816 in FIG. 12. The guillotine might be of the form of cutter wheel 566 described earlier.

A light source (not shown) might be provided in association with lens 802 to illuminate the external ear cavity for viewing through eyepiece 801 and to be received by image sensor 806.

In use, a doctor holding handle 803 of otoscope 800 would use eyepiece 801 to view the external ear cavity after inserting the lens 802 therein. When ready, the trigger 807 can be depressed to activate the print engine controller to print an image stored in memory 815. This would in turn activate the micro-controller 807 to activate the media transport 810 and guillotine 812. A printed image 816 having passed out of handle 803 via slot 804 would then be available as a permanent record and for viewing by the doctor and patient.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein. It will further be understood that any reference herein to known prior art does not, unless the contrary indication appears, constitute an admission that such prior art is commonly known by those skilled in the art to which the invention relates.

We claim:

1. A hand-held otoscope comprising:
   a substantially cylindrical handle;
   an image sensor to receive image data of an external ear cavity after inserting a lens therein, the image sensor positioned at an end of the handle;
   a trigger provided in the handle of the otoscope;
   an image memory to store the image data upon activation of the trigger;
   a roll of print media mounted in the handle;
   an ink supply within a core of the roll of print meida;
   a media transportation mechanism for transporting print media from the roll upon activation of the trigger;
   a pagewidth print head extending longitudinally within the handle of the otoscope for printing a graphic image using ink supplied from the ink supply and the image data onto the transported print media upon activation of the trigger;
   a guillotine mechanism for severing a printed image from the transported print media; and,
   a print engine controller which receives the image data from the image memory and which controls the media transportation mechanism, print head and guillotine mechanism upon activation of the trigger.

2. The otoscope of claim 1 wherein associated with the image sensor and print engine controller is a micro-control circuit adapted to control a motor driver for the media transportation and guillotine mechanisms.

3. The otoscope of claim 1 wherein the print head is an ink jet print head.

4. The otoscope of claim 1 including a light source for illuminating the external ear cavity of a patient for viewing by a doctor with the otoscope.

* * * * *